United States Patent [19]

Junino et al.

[11] Patent Number: 5,449,805
[45] Date of Patent: Sep. 12, 1995

[54] INTERMEDIATES FOR PREPARING ALKYLAMINO MERCAPTOALKYLAMIDES

[75] Inventors: Alex Junino, Livry Gargan; Gerard Malle, Villiers Sur Morin; Bernadette Luppi, Sevran, all of France

[73] Assignee: L'Oreal, Paris, France

[21] Appl. No.: 204,495

[22] Filed: Mar. 2, 1994

Related U.S. Application Data

[62] Division of Ser. No. 883,870, May 15, 1992, Pat. No. 5,334,377.

[30] Foreign Application Priority Data

May 17, 1991 [FR] France ................. 91 06029

[51] Int. Cl.$^6$ ............................................ C07C 327/30
[52] U.S. Cl. ...................................... 558/252; 558/256
[58] Field of Search ............................... 558/252, 256

[56] References Cited

U.S. PATENT DOCUMENTS 4,816,482 3/1989 Oiry et al. ..................... 514/513

FOREIGN PATENT DOCUMENTS 0131500 1/1985 European Pat. Off. .

OTHER PUBLICATIONS

Chemical Abstracts, vol. 92, 1980, p. 566, Abstract No. 163592h.
Journal of Medicinal Chemistry, vol. 29, 1986, pp. 2217-2225, Oiry et al "Synthesis and Radioprotective Activity of New Cysteamine and Cystamine Derivatives".
Chemical Abstracts, vol. 66, 1967, p. 5382, Abstract No. 55749u.
European Journal of Medicinal Chemistry, vol. 23, 1988, pp. 257-266, Fatome et al: "Etude de Germathiazolidines et de Dithioacetals Germanies Derives de la Cysteamine et Methylcysteamine N-Substitutes: Synthese et Activite Radioprotectrice".
Chemical Abstracts, vol. 83, 1975, p. 512, Abstract No. 178363x.
Journal of Pharmaceutical Sciences, vol. 53, 1964, pp. 906-908, Foye et al: "Antiradiation Compounds V Alpha-Amino Acid Esters of 2-Mercaptoethylamine".
Oiry et al, Chemical Abstracts, vol. 118 (1992) 234432z.
Junino et al, Chemical Abstracts, vol. 115 (1991) 214513m.
Korshunov et al, Chemical Abstracts, vol. 79 (1973) 115087g.
Chavin et al, Chemical Abstracts, vol. 68 (1968) 113155b.
Foye et al, Chemical Abstracts, vol. 62 (1965) 14811b.

*Primary Examiner*—Richard L. Raymond
*Attorney, Agent, or Firm*—Cushman Darby & Cushman

[57] ABSTRACT

Alkylamino-mercaptoalkylamides have the formula $$HS-A-NH-CO-\underset{R_1}{CH}-(CH_2)_m-N\underset{R_3}{\overset{R_2}{\diagup}} \quad (I)$$

wherein
A represents the divalent radical —$(CH_2)_n$—, wherein n is a whole number ranging from 2 to 5, or the divalent radical —$(CH_2)_2$—O—$(CH_2)_2$—,
m is 0, 1 or 2,
$R_1$ represents hydrogen or linear or branched lower alkyl having 1-5 carbon atoms,
$R_2$ and $R_3$, each independently, represent hydrogen or a linear or branched lower alkyl having 1-4 carbon atoms with the proviso that $R_2$ and $R_3$ are not hydrogen simultaneously and the salts of the compound of formula I as well as the corresponding disulfides with the exclusion of the disulfide in which A=—$(CH_2)_2$—, m=0, $R_1$ and $R_2$=H and $R_3$=—$C_2H_5$. The compound of formula I is used as a reducing agent in a cosmetic composition for the permanent deformation of hair.

2 Claims, No Drawings

INTERMEDIATES FOR PREPARING ALKYLAMINO MERCAPTOALKYLAMIDES

This is a division of application Ser. No. 07/883,870, filed May 15, 1992, now U.S. Pat. No. 5,334,377.

The present invention relates to new alkylamino mercaptoalkylamides or one of their cosmetically acceptable salts and to their use, as reducing agents, in a process for the permanent deformation of hair.

The technique to effect the permanent deformation of hair comprises, in a first stage, effecting the opening of the disulfide bonds of keratin (cystine) using a composition containing a reducing agent (reduction stage) and then, after having preferably rinsed the hair, reconstituting in a second stage, the said disulfide bonds by applying, on the hair under tension, an oxidizing composition, (oxidation stage, also called the fixation stage), so as to impart to the hair the desired form. This technique permits indifferently, to effect either the waving of the hair or uncurling or uncrisping of the hair.

Compositions to carry out the first stage of a permanent operation are generally provided in the form of lotions, creams, gels or powders to be diluted in a liquid support and preferably contain, as the reducing agent, a mercaptan.

Among these latter, those currently employed, are thioglycolic acid and thiolactic acid or a mixture of these acids, as well as their esters, for example, the monothioglycolate of glycerol or glycol.

These reducing agents which are particularly effective to reduce the disulfide bonds of keratin include, principally, thioglycolic acid which can be considered as the product of choice in permanent waving operations. It provides a reduction rate of about 50 percent.

However, these reducing agents exhibit a major disadvantage in that they emit bad odors.

With a view to remedy this disadvantage, there is generally employed a perfume so as to mask these odors.

After significant research, it has now been observed, in a quite unexpected and surprising manner, that by using a new class of alkylamino-mercaptoalkylamides or their cosmetically acceptable salts, it was possible to remedy the disadvantages of prior art reducing agents.

The reducing agents of the compositions in accordance with the invention exhibit not only the advantage of being practically void of odor but they also provide a yield, a liveliness and beauty of curling greater than that obtained in accordance with current techniques using, for example, thioglycolic acid.

The present invention thus related to, as a new industrial product, alkylamino-mercaptoalkylamides having the following general formula (I)

$$HS-A-NH-CO-CH(R_1)-(CH_2)_m-N(R_2)(R_3) \quad (I)$$

wherein

A represents the divalent radical $-(CH_2)_n-$, wherein n represents a whole number ranging from 2 to 5, or the divalent radical $-(CH_2)_2-O-(CH_2)_2-$, m is equal to 0, 1 or 2, $R_1$ represents hydrogen or linear or branched lower alkyl having 1–5 carbon atoms, $R_2$ and $R_3$, each independently, represent hydrogen or linear or branched lower alkyl having 1–4 carbon atoms, with the proviso that $R_2$ and $R_3$ are not hydrogen simultaneously, and the salts of said compounds of formula (I).

Among the cosmetically acceptable salts of the compounds of formula (I), those particularly preferred are the hydrochlorides, hydrobromides, citrates, oxalates and acetates.

By lower alkyl having either 1–4 or 1–5 carbon atoms is meant methyl, ethyl, propyl, isopropyl, butyl, isobutyl, 2-methylbutyl or pentyl.

Principal among the preferred compounds having the general formula (I) are the following:

2-dimethylamino N-(2-mercaptoethyl) acetamide,
2-dimethylamino N-(3-mercaptopropyl) acetamide,
2-dimethylamino N-(5-mercaptopentyl) acetamide,
2-dimethylamino N-[2'-(2-mercaptoethoxy)ethyl] acetamide,
2-diethylamino N-(2-mercaptoethyl) acetamide,
2-diethylamino N-(3-mercaptopropyl) acetamide,
2-diethylamino N-(5-mercaptopentyl) acetamide,
2-diethylamino N-[2'-(2-mercaptoethoxy) ethyl] acetamide,
2-methylamino N-(2-mercaptoethyl) acetamide,
2-methylamino N-(3-mercaptopropyl) acetamide,
2-methylamino N-(5-mercaptopentyl) acetamide,
2-methylamino N-[2'-(2-mercaptoethoxy) ethyl] acetamide,
2-ethylamino N-(2-mercaptoethyl) acetamide,
2-ethylamino N-(3-mercaptopropyl) acetamide,
2-ethylamino N-(5-mercaptopentyl) acetamide,
2-ethylamino N-[2'-(2-mercaptoethoxy) ethyl] acetamide,
2-ethylamino-2-methylamino N-(2-mercaptoethyl) acetamide,
2-propylamino N-(2-mercaptoethyl) acetamide,
2-isopropylamino N-(2-mercaptoethyl) acetamide,
2-butylamino N-(2-mercaptoethyl) acetamide,
2-ethylmethylamino N-(2-mercaptoethyl) acetamide,
3-dimethylamino N-(2-mercaptoethyl) propionamide,
3-dimethylamino N-(3-mercaptopropyl)propionamide,
3-dimethylamino N-(5-mercaptopentyl) propionamide,
3-dimethylamino N-[2'-(2-mercaptoethoxy)ethyl] propionamide,
3-methylamino N-(2-mercaptoethyl) propionamide,
3-methylamino N-(3-mercaptopropyl) propionamide,
3-methylamino N-(5-mercaptopentyl) propionamide,
3-methylamino N-[2'-(2-mercaptoethoxy) ethyl] propionamide,
2-dimethylamino N-(2-mercaptoethyl) propionamide,
2-dimethylamino N-(3-mercaptopropyl) propionamide,
2-dimethylamino N-(5-mercaptopentyl) propionamide,
2-dimethylamino N-[2'-(2-mercaptoethoxy) ethyl] propionamide,
2-methylamino N-(2-mercaptoethyl) propionamide,
2-ethylamino N.-(2-mercaptoethyl) propionamide,
2-isopropylamino N-(2-mercaptoethyl) propionamide,
2-methylamino-N-(2-mercaptoethyl) butanamide,
4-dimethylamino N-(2-mercaptoethyl) butanamide,
4-dimethylamino N-(3-mercaptopropyl) butanamide, 4-dimethylamino N-(5-mercaptopentyl) butanamide,
4-dimethylamino N-[2'-(2-mercaptoethoxy) ethyl] butanamide,
4-methylamino N-(2-mercaptoethyl) butanamide,
4-ethylamino N-(2-mercaptoethyl) butanamide,
2-dimethylamino-3-methyl N-(2-mercaptoethyl) butanamide,
2-dimethylamino-4-methyl N-(2-mercaptoethyl) pentamide,
2-methylamino-4-methyl N-(2-mercaptoethyl) pentamide,
2-dimethylamino-3-methyl N-(2-mercaptoethyl) pentamide, and
2-methylamino-3-methyl N-(2-mercaptoethyl) pentanamide.

The present invention also relates to a process for preparing the alkylamino-mercapto alkylamides according-to the invention. This process comprises reacting an aminothiol (1) with an acid halide of an alkylamino acid (2) so as to obtain a thioester of general formula (II) which is then rearranged into the alkylamino-mercaptoalkylamide of general formula (I) by treatment with a base, in accordance with the following reaction scheme:

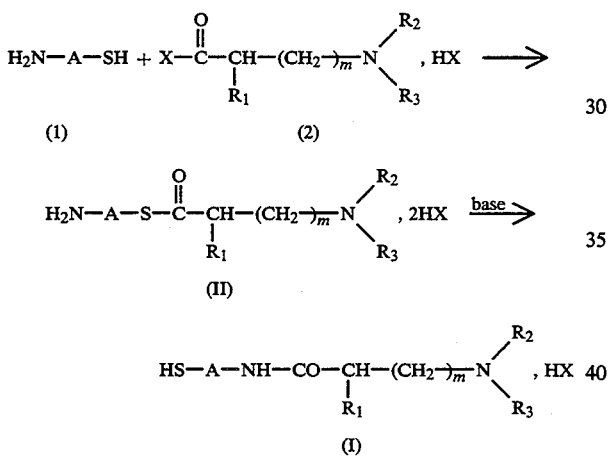

wherein
A, $R_1$, $R_2$, $R_3$ and m have the same meanings given above for general formula (I), and
X represents Cl or Br.

The aminothiols (1) and the acid halides of alkylaminoacids (2) are prepared following known methods, the acid halides being obtained by a method analogous to that described, for example, in E. Ficher, Chem. Ber. 38, 2914–2934, (1905). The reaction between (1) and (2) is conducted under an inert atmosphere in an inert solvent such as, for example, dichloromethane, 1,2-dichloroethane, 1,1,1,-trichloroethane, chloroform, acetonitrile, carbon tetrachloride, toluene, dioxane, tetrahydrofuran, 1,2-dimethoxyethane, N-methylpyrrolidone, dimethylformamide, dimethylacetamide, or a mixture of these solvents, and, depending on the boiling point of the solvent, at a temperature between 40 and 110° C. The reaction time generally is less than 5 hours.

The rearrangement of the thioesters of general formula (II) into the alkylamino-mercaptoalkylamides of general formula (I) is carried out in an aqueous or hydroalcoholic medium at ambient temperature and under an inert atmosphere in the presence of at least one equivalent of a base such as ammonia, alkaline metal hydroxides or even a tertiary amine such as triethylamine or triethanolamine.

The present invention also relates to a reducing composition for the first stage of an operation for the permanent deformation of hair comprising, in a cosmetically acceptable vehicle, at least one alkylamino mercaptoalkylamide of general formula (I), as a reducing agent.

In the compositions according to the invention, the reducing agent of general formula (I) is generally present in an amount ranging from 2 to 30 and preferably between 5 and 25 percent by weight based on the total weight of the reducing composition.

The pH of the composition is preferably between 4.5 and 11 and more particularly between 6 and 10 and is obtained using an alkaline agent such as, for example, ammonia, monoethanolamine, diethanolamine, triethanolamine, an alkaline or ammonium carbonate or bicarbonate, an alkaline hydroxide or using an acidifying agent such as, for example, hydrochloric acid, acetic acid, lactic acid, oxalic acid or boric acid.

The reducing composition can also contain other reducing agents such as, for example, thioglycolic acid, glycerol or glycol monothioglycolate, cysteamine and its $C_1$–$C_4$ acyl derivatives such as, for example, N-acetylcysteamine or N-propionyl cysteamine, cysteine, N-acetylcysteine, N-mercaptoalkylamides of sugars such as N-(2-mercaptoethyl) gluconamide, S-mercaptopropionic acid and its derivatives, thiolactic acid, thiomalic acid, pantetheine, thioglycerol, the sulfites or bisulfites of an alkali or alkaline earth metal, N-(mercaptoalkyl) ω-hydroxy-alkylamides described in EP 354 835, the N-mono- or N,N-dialkylmercapto-4-butyramides described in EP 368 763, the aminomercapto alkylamines described in EP 403 267 and the derivatives of N-(mercaptoalkyl) succinamic acids or N-(mercaptoalkyl) succinimides described in EP 465 342.

The reducing composition can also contain various ingredients such as, for example, cationic polymers such as those employed in the compositions described in French patents No. 79.32078 and 80.26421 or even cationic polymers of the ionene type such as those employed in the compositions disclosed in French patent No. 82.17364, softening agents and principally quaternary ammonium derivatives of lanolin, protein hydrolyzates, waxes, opacifying agents, perfumes, dyes, nonionic or cationic surfactants, alcohols such as ethanol, propanol, isopropanol, 1,2-propanediol, 1,2-butanediol or glycerol, treating agents or even penetration agents such as urea, pyrrolidone or thiomorpholinone.

The reducing composition according to the invention can also be of the exothermic type, that is to say, provoking a certain amount of heat during application on the hair, which is agreeable to the person undergoing to the first stage of the permanent or uncurling of the hair.

The vehicle for the compositions according to the invention is preferably water or a hydroalcoholic solution of a lower alcohol such as ethanol, isopropanol or butanol.

When the compositions are intended for a hair uncurling or uncrisping operation the reducing composition is preferably in the form of a cream so as to maintain the hair as rigid or stiff as possible. These creams are provided in form of "heavy" emulsions, for example, those based on glyceryl stearate, glycol stearate, self-emulsifiable waxes, fatty alcohols, etc. Liquids or gels containing thickening agents, such as carboxyvinyl polymers or copolymers which "glue" the hair can also be employed so as to maintain the hair in a smooth position during the setting period.

In accordance with a particular embodiment of the invention, the reducing compounds of general formula (I) can be formed in situ at the time of use starting with their thioester precursors having the following general formula (II):

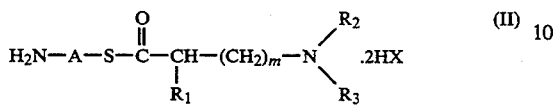

wherein
A, $R_1$, $R_2$, $R_3$ and m have the same meanings as those given above for formula (I), and
X is Cl or Br.

It has been noted, in effect, that in the presence of a base such as ammonia, monoethanolamine, diethanolamine, triethanolamine, soda or potash, these thioester precursor are transformed almost instantaneously and quantitatively into the corresponding thiols of general formula (I).

In accordance with this embodiment, the thioester precursor in the solid state, preferably in the form of a powder, is mixed at the time of use with a basic aqueous solution having a pH between 8 and 10, optionally containing various ingredients such as those mentioned above.

The pH of the composition is then adjusted, if necessary, using an alkaline agent or an acidifying agent such as those mentioned previously.

Thus, the present invention also relates to, as new products, thioesters having general formula (II), above, as precursors of the alkylamino mercaptoalkylamides of general formula (I).

Principal among these thioesters are the following compounds:
the dihydrochloride of 2-aminoethyl N,N-dimethyl thioglycinate,
the dihydrochloride of 3-aminopropyl N,N-dimethyl thioglycinate,
the dihydrochloride of 5-aminopentyl N,N-dimethyl thioglycinate,
the dihydrochloride of 2'-(2-aminoethoxy) ethyl N,N-dimethyl thioglycinate,
the dihydrochloride of 2-aminoethyl N,N-diethyl thioglycinate,
the dihydrochloride of 3-aminopropyl N,N-diethyl thioglycinate,
the dihydrochloride of 5-aminopentyl N,N-diethyl thioglycinate,
the dihydrochloride of 2'-(2-aminoethoxy) ethyl N,N-ethyl thioglycinate,
the dihydrochloride of 2-aminoethyl N-methyl thioglycinate,
the dihydrochloride of 3-aminopropyl N-methyl thioglycinate,
the dihydrochloride of 5-aminopentyl N-methyl thioglycinate,
the dihydrochloride of 2'-(2-aminoethoxy) ethyl N-methyl thioglycinate,
the dihydrochloride of 2-aminoethyl N-ethyl thioglycinate,
the dihydrochloride of 3-aminopropyl N-ethyl thioglycinate,
the dihydrochloride of 5-aminopentyl N-ethyl thioglycinate,
the dihydrochloride of 2'-(2-aminoethoxy) ethyl N-ethyl thioglycinate,
the dihydrochloride of 2-aminoethyl N-ethyl-N-methyl thioglycinate,
the dihydrochloride of 2-aminoethyl N-propyl thioglycinate,
the dihydrochloride of 2-aminoethyl N-isopropyl thioglycinate,
the dihydrochloride of 2-aminoethyl N-butyl thioglycinate,
the dihydrochloride of 2-aminoethyl 3-dimethyl amino thiopropionate,
the dihydrochloride of 3-aminopropyl-3-dimethylamino thiopropionate,
the dihydrochloride of 5-aminopentyl 3-dimethylamino thiopropionate,
the dihydrochloride of 2'-(2-aminoethoxy) ethyl 3dimethylamino thiopropionate,
the dihydrochloride of 2-aminoethyl 3-methylamino thiopropionate,
the dihydrochloride of 3-aminopropyl 3-methylamino thiopropionate,
the dihydrochloride of 5-aminopentyl 3-methylamino thiopropionate,
the dihydrochloride of 2'-(2-aminoethoxy) ethyl 3methylamino thiopropionate,
the dihydrochloride of 2-aminoethyl N,N-dimethyl thioalaninate,
the dihydrochloride of 3-aminopropyl N,N-dimethyl thioalaninate,
the dihydrochloride of 5-aminopentyl N,N-dimethyl thioalaninate,
the dihydrochloride of 2'-(2-aminoethoxy) ethyl N,N-dimethyl thioalaninate,
the dihydrochloride of 2-aminoethyl N-methyl thioalaninate,
the dihydrochloride of 2-aminoethyl N-ethyl thioalaninate,
the dihydrochloride of 2-aminoethyl N-isopropyl thioalaninate,
the dihydrochloride of 2-aminoethyl 2-methylamino thiobutyrate,
the dihydrochloride of 2-aminoethyl 4-dimethyl aminothiobutyrate,
the dihydrochloride of 3-aminopropyl 4-dimethylamino thiobutyrate,
the dihydrochloride of 5-aminopentyl 4-dimethylamino thiobutyrate,
the dihydrochloride of 2'-(2-aminoethoxy) ethyl 4dimethylamino thiobutyrate,
the dihydrochloride of 2-aminoethyl 4-methylamino thiobutyrate,
the dihydrochloride of 2-aminoethyl 4-ethylamino thiobutyrate,
the dihydrochloride of 2-aminoethyl N,N-dimethylamino thiovalinate,
the dihydrochloride of 2-aminoethyl N,N-dimethylamino thioleucinate,
the dihydrochtoride of 2-aminoethyl N-methylamino thioleucinate,
the dihydrochloride of 2-aminoethyl N,N-dimethylamino thioisoleucinate,
the dihydrochloride of 2-aminoethyl N-methylamino thioisoleucinate, the dihydrochloride of 2-aminoethyl thiopipecolinate and the dihydrochloride of 2-aminoethyl hexahydroisothionicotinate.

The compositions according to the invention can also be in a form called "self-neutralizing" or even "self-regulated" and in this case, the reducing compound of general formula (I) is combined with at least one disulfide either known for its use in a reducing composition for a self-neutralizing permanent or derived from a compound of general formula (I) or one of its salts and corresponds to the following general formula (III):

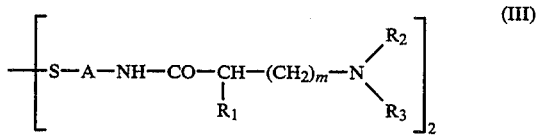

wherein

A, $R_1$, $R_2$, $R_3$ and m have the same meanings as those given for general formula (I) with the exclusion of the compounds of formula (III) is which:
A=—$(CH_2)_2$—, m=0,
$R_1$ and $R_2$=H and $R_3$=—$C_2H_5$.

The disulfide can also be provided in the form of a cosmetically acceptable salt.

Among the known disulfides, there can principally be mentioned dithioglycolic acid, dithioglycerol, cystamine, N,N'-diacetyl-cystamine, cystine, pantethine, the disulfides of N-(mercaptoalkyl)ω-hydroxyalkylamides described in EP 354,835 and the disulfides of N-mono or N,N-dialkylmercapto-4 butyramides described in EP 368.763, the disulfides of aminomercaptoalkylamides described in EP 403,267, and the disulfides of the derivatives of N-(mercaptoalkyl) succinamic acids or N-(mercaptoalkyl) succinimides described in EP 465 342.

Among the disulfides derived from a compound of general formula (I) and corresponding to general formula (III) there can principally be mentioned:

N,N'-(2,1-dithiodiethanediyl) bis [2-dimethyl amino acetamide],

N,N'-(2,1-dithiodiethanediyl) bis [2-dimethyl amino propionamide],

N,N'-(2,1-dithiodiethanediyl) bis [3-dimethyl amino propionamide],

N,N'-(2,1-dithiodiethanediyl) bis [4-dimethyl amino butyramide],

N,N'-(2,1-dithiodiethanediyl) bis [2-methyl amino acetamide],

N,N'-[dithiobis(trimethylene)] bis [2-dimethyl amino acetamide],

N,N'-[dithiobis (pentamethylene)] bis [2-dimethyl amino acetamide],

N,N'-[dithiobis (2-ethoxyethyl)] bis [2-dimethyl amino acetamide],

N,N'-(2,1-dithiodiethanediyl) bis [3-methyl amino propionamide],

N,N'-)(2,1-dithiodiethanediyl) bis [2-diethyl amino acetamide], and

N,N'-(2,1-dithiodiethanediyl) bis [2-ethyl amino acetamide].

In the self-neutralizing compositions the disulfide is generally present in a molar ratio of 0.5 to 2.5 and preferably from 1 to 2 relative to the compounds of general formula (I) or its salts (see U.S. Patent 3,768,490).

The disulfides of general formula (III) are obtained by oxidation of the compounds of general formula (I) either in air or by using known oxidants such as, for example, $H_2O_2$ in the presence, optionally, of metallic salts such as, for example, ferrous salts.

The present invention also relates to a process for the permanent deformation of hair comprising, in a first stage, reducing the disulfide bonds of keratin by applying to the hair for a period of about 5 to 60 minutes, a reducing composition, such as defined above, and then in a second stage, reforming the said bonds by applying to the hair an oxidizing composition or optionally by letting the oxygen of the air act on the hair.

The present invention also relates to a process for waving the hair in which a reducing composition, such as defined above, is applied to moistened hair previously rolled up on rollers having a diameter of 4 to 20 mm. The composition can optionally be applied while rolling up the hair. The reducing composition is then permitted to act on the hair for a period of time ranging from 5 to 60 minutes, preferably 5 to 30 minutes. The hair is then thoroughly rinsed, after which there is applied to the rolled up hair, an oxidizing composition so as to reform the disulfide bonds of the keratin during a setting period of 2 to 10 minutes. After having removed the rollers, the hair is thoroughly rinsed.

The oxidizing composition, or oxidant, is of the type currently employed and contains as the oxidizing agent $H_2O_2$, an alkaline bromate, a persalt, a polythionate or a mixture of an alkaline bromate and a persalt. The concentration of $H_2O_2$ can vary from 1 to 20 volumes and preferably from 1 to 10 volumes; the concentration of alkaline bromate, from 2 to 12 percent; and that of the persalt from 0.1 to 15 percent by weight relative to the total weight of the oxidizing composition. The pH of the oxidizing composition is generally between 2 and 10. This oxidation can be carried out immediately or be deferred.

The present invention also relates to a process for uncurling or uncrisping the hair which comprises applying to the hair a reducing composition, in accordance with the invention, submitting the hair to a mechanical deformation so as to fix the hair in a new form, by a smoothing the hair with a large tooth comb, with the back of a comb or with the hand. After a setting period of 5 to 60 minutes, particularly 5 to 30 minutes, the hair is again smoothened and then carefully rinsed. There is then applied to the hair an oxidant or fixing agent such as defined above which is permitted to act on the hair for about 2 to 10 minutes. The hair is then thoroughly rinsed.

There are now given as an illustration and without any limiting character, several examples of the preparation of the compounds according to the invention, as well as reducing compositions according to the invention and their use in a process for the permanent deformation of hair.

EXAMPLES OF PREPARATION

Example 1

Preparation of the Dihydrochloride of 2-Aminoethyl N,N-Dimethyl Thioglycinate

To a suspension of 20 g (0.126 mole) of the hydrochloride of N,N-dimethylglycine acid chloride in 120 cm³ of anhydrous acetonitrile, there are added, under an inert atmosphere and with stirring, 14.38 mg (0.126 mole) of cysteamine hydrochloride. The mixture is then heated 3 hours at 75°-80° C. After cooling to +5° C., the crude thioester (29.6 g) is filtered off and purified by recrystallization in methanol. After drying under a vacuum at 40°–50° C., 19.5 g of the dihydrochloride of 2-aminoethyl N,N-dimethyl thioglycinate are obtained in the form of a white solid whose melting point: is 191°–193° C.

The NMR$^1$H 250 MHz spectrum conforms to the expected structure as does the chloride dosage (Found—8.6 meq/g; Calculated 8.5 meq/g).

Elemental analysis: $C_6H_{14}N_2OS \cdot 2HCl$

|  | C % | H % | N % | O % | S % | Cl % |
| --- | --- | --- | --- | --- | --- | --- |
| Calculated | 30.64 | 6.86 | 11.91 | 6.80 | 13.63 | 30.15 |
| Found | 30.30 | 6.94 | 10.79 | 6.71 | 13.56 | 30.00 |

Example 2

Preparation of the Hydrochloride of 2-Dimethylamino-N-(2-Mercaptoethyl) Acetamide To a suspension of 11.76 g (0.05 mole) of the dihydrochloride of 2-aminoethyl N,N-dimethyl thioglycinate, obtained in Example 1, in 100 cm$^3$ of isopropanol, there are slowly added, over a period of about 10 minutes, at ambient temperature under an inert atmosphere and with stirring, 41 g of a 5% aqueous ammonia solution. The resulting solution is then evaporated to dryness under reduced pressure. 50 cm$^3$ of dry chloroform are added and the ammonium chloride is filtered off on a fritted glass. The filtrate is evaporated to dryness under reduced pressure. A gel is obtained which slowly crystallizes at ambient temperature. The resulting crystals are taken up in 40 cm$^3$ of anhydrous ethyl acetate, filtered and dried under a vacuum at 50° C.

9.4 g of the hydrochloride of 2-dimethylamino N-(2-mercaptoethyl) acetamide are obtained in the form of a white solid whose melting point is 76° C.

The NMR$^1$H 250 MHz and $^{13}$C spectra conform to the expected structure.

Elemental analysis: $C_6H_{14}N_2OS \cdot HCl$

|  | C % | H % | N % | O % | S % | Cl % |
| --- | --- | --- | --- | --- | --- | --- |
| Calculated | 36.27 | 7.61 | 14.10 | 8.05 | 16.14 | 17.84 |
| Found | 36.26 | 7.66 | 14.30 | 8.50 | 16.00 | 17.87 |

Example 3

Preparation of N,N'-(2,1-Dithiodiethanediyl) Bis [2-Dimethylamino Acetamide]

(a) the hydrochloride of N,N'-(2,1-dithiodiethanediyl) bis [2-dimethylamino acetamide]

To a solution of 2 g (0.01 mole) of the hydrochloride of 2-dimethyl amino N-(2-mercaptoethyl) acetamide, obtained in Example 2, in 15 cm$^3$ of absolute alcohol, there is slowly added 0.55 cm$^3$ (5 mmoles) of 110 volume H$_2$O$_2$ while maintaining the temperature lower than 25° C. A trace of ferrous sulfate is then added and the mixture is stirred for 6 hours at ambient temperature. The reaction medium is concentrated under reduced pressure. 30 cm$^3$ of toluene are added to the residue and the mixture is again evaporated to dryness.

After drying under a vacuum at ambient temperature, 1.9 g of the hydrochloride of N,N'-(2,1-dithiodiethanediyl) bis [2-dimethylamino acetamide] are obtained in the form of a pulverulent, very hygroscopic white solid.

(b) N,N'-(2,1-dithiodiethanediyl) bis [2-dimethylamino acetamide]

1.58 g (4 mmoles) of the compound obtained in (a) above are dissolved in 20 ml of water, 0.67 g (8 mmoles) of sodium bicarbonate is added and the mixture is evaporated to dryness under reduced pressure. The residue is taken up in 20 ml of ethanol and the sodium chloride is separated by filtration. The filtrate is evaporated to dryness under reduced pressure. After recrystallization in acetone and drying under a vacuum at ambient temperature 1.13 g of N,N'-(2,1-dithiodiethanediyl) bis [2-dimethylamino acetamide] are obtained in the form of a white solid whose melting point in 100° C.

The NMR$^1$H 250 MHz spectrum conforms to the expected structure.

|  | C % | H % | N % | O % | S % |
| --- | --- | --- | --- | --- | --- |
| Calculated | 44.69 | 8.13 | 17.37 | 9.92 | 19.89 |
| Found | 44.63 | 8.22 | 17.04 | 9.97 | 19.64 |

Example 4

Preparation of the Dihydrochloride of 2-Aminoethyl N,N-Diethyl Thioglycinate To a suspension of 7 g (37 mmoles) of the hydrochloride of N,N-diethylglycine acid chloride in 40 cm$^3$ of anhydrous acetonitrile, there are added, under an inert atmosphere and with stirring, 4.27 g (37.5 mmoles) of cysteamine hydrochloride. The mixture is then heated for 3 hours at reflux.

After cooling the reaction medium to +5° C., the crude thioester (9 g) is filtered and then purified in 20 cm$^3$ of boiling ethyl alcohol. The mixture is cooled to +10° C. and filtered. After drying under a vacuum at 50° C., 6.6. g of the dihydrochloride of 2-aminoethyl N,N-diethylthioglycinate are obtained in the form of a white solid whose melting point (with decomposition) is about 200° C.

The NMR$^{13}$C spectrum conforms to the expected structure as does the chloride dosage (Found—7.64 meq/g; Calculated—7.60 meg/g).

Elemental analysis: $C_8H_{18}N_2OS \cdot 2HCl$

|  | C % | H % | N % | O % | S % | Cl % |
| --- | --- | --- | --- | --- | --- | --- |
| Calculated | 36.50 | 7.66 | 10.64 | 6.08 | 12.18 | 26.94 |
| Found | 36.30 | 7.61 | 10.68 | 6.18 | 12.03 | 27.16 |

Example 5

Preparation of the Hydrochloride of 2-Diethyl Amino N-(2-Mercaptoethyl) Acetamide To as suspension of 3 g (11.4 mmoles) of the dihydrochloride of 2-aminoethyl N,N-diethyl thioglycinate, obtained in Example 3, in 20 cm$^3$ of isopropanol, there are slowly added, over a period of about 20 minutes, at ambient temperature under an argon atmosphere and with stirring, 8.8 cm$^3$ of a 5% aqueous ammonia solution.

The resulting solution is evaporated to dryness under reduced pressure. The residue is dispersed in 40 cm$^3$ of ethanol, cooled to 0° C. and the ammonium chloride is filtered on fritted glass. The filtrate is evaporated to dryness under reduced pressure and dried under a vacuum at 40° C. 2.4 g of the hydrochloride of 2-.diethylamino N-(2-mercaptoethyl) acetamide are obtained in the form of a colorless oil.

The NMH¹H 250 MHz spectrum conforms to the expected structure. The thiol dosage by iodometry in an acid medium also conforms: Found 4.40 meq/g—Calculated—4.41 meq/g.

Example 6
Preparation of the Dihydrochloride of 2-Aminoethyl N-Methyl Thioglycinate A mixture of 63.4 g (0.44 mole) of the hydrochloride of sarcosine acid chloride and 50 g (0.44 mole) of cysteamine hydrochloride in 200 cm³ of anhydrous acetonitrile is stirred for 2 hours at reflux under an argon atmosphere.

After cooling to ±5° C., the crude thioester is separated by decanting the solvent, then purified by recrystallization in an ethanol/methanol mixture. After drying under a vacuum at 40° C., 46 g of the dihydrochloride of 2-aminoethyl N-methyl thioglycinate are obtained in the form of a white solid whose melting point (decomposition) is about 220° C.

The NMR¹³C spectrum conforms to the expected structure as does the chloride dosage (Found—9.06 meq/g; calculated—9.04 meq/g).

Elemental analysis: $C_5H_{12}N_2OS.2HCl$

|  | C % | H % | N % | O % | S % | Cl % |
|---|---|---|---|---|---|---|
| Calculated | 27.16 | 6.38 | 12.67 | 7.23 | 14.50 | 32.06 |
| Found | 27.20 | 6.44 | 12.48 | 7.60 | 14.22 | 31.80 |

Example 7
Preparation of the Dihydrochloride of 2-Aminoethyl N-Ethyl Thioglycinate A suspension of 5 g (31.6 mmoles) of the hydrochloride of N-ethylglycine acid chloride and 3.6 g (31.7 mmoles) of cysteamine hydrochloride in 50 cm³ of anhydrous acetonitrile is brought to the reflux with stirring and under an inert atmosphere for 2 hours.

After cooling to +5° C., the solvent is removed by decanting and the crude thioester is recrystallized in an ethanol/methanol mixture. After drying under a vacuum at 40° C., 3.6 g of the dihydrochloride of 2-aminoethyl N-ethyl thioglycinate are obtained in the form of a white solid whose melting point (decomposition) is close to 215° C.

The NMR¹³C spectrum conforms to the expected structure as does the chloride dosage (Found—8.6 meq/g; calculated—8.5 meq/g).

Elemental analysis: $C_6H_{14}N_2OS.2HCl$

|  | C % | H % | N % | O % | S % | Cl % |
|---|---|---|---|---|---|---|
| Calculated | 30.64 | 6.86 | 11.91 | 6.80 | 13.63 | 30.15 |
| Found | 30.32 | 6.95 | 11.73 | 6.90 | 13.40 | 29.80 |

Example 8
Preparation of the Dihydrochloride of 2-Aminoethyl N-Ethyl N-Methyl Thioglycinate A suspension of 106 g (0.616 mole) of the hydrochloride of N-ethyl N-methyl glycine acid chloride and 70 g (0.616 mole) of cysteamine hydrochloride in 400 cm³ of anhydrous acetonitrile is stirred for 5 hours at reflux under an inert atmosphere.

After cooling to 20° C., the crude thioester is filtered (144.3 g), then purified by recrystallization in a 40/60 ethanol/methanol mixture. After drying under a vacuum at 50° C., 110.5 g of the dihydrochloride of 2-aminoethyl N-ethyl N-methyl thioglycinate are obtained in the form of a white solid whose melting point (decomposition) is about 210° C.

The NMR¹³C spectrum conforms to the expected structure as does the chloride dosage (Found—8.10 meq/g; Calculated—8.02 meq/g).

Elemental analysis: $C_7H_{16}N_2OS.2HCl$

|  | C % | H % | N % | O % | S % | Cl % |
|---|---|---|---|---|---|---|
| Calculated | 33.74 | 7.28 | 11.24 | 6.42 | 12.87 | 28.45 |
| Found | 33.74 | 7.38 | 10.78 | 6.72 | 12.36 | 27.90 |

Example 9
Preparation of the Hydrochloride of 2-Ethylmethylamino N-(2-Mercaptoethyl) Acetamide To a suspension of 30 g (0.12 mole) of the dihydrochloride of 2-aminoethyl N-ethyl N-methyl thioglycinate, obtained in Example 7, in 150 cm³ of isopropanol, stirred under argon at ambient temperature, there are slowly added, over a period of about 30 minutes, 126.4 g of a 5% aqueous ammonia solution.

The resulting solution is evaporated to dryness under reduced pressure. 100 cm³ of ethyl alcohol are added and the mixture is again evaporated to dryness under reduced pressure.

The residue is taken up in 150 cm³ of ethanol with stirring, cooled to 0° C. and the ammonium chloride is filtered off on fritted glass. The filtrate is evaporated to dryness and the residue is taken up in 200 cm³ of dry chloroform. This mixture is then filtered on fritted glass so as to separate the residual ammonium chloride. The filtrate is then evaporated to dryness and dried under a vacuum at 50° C. in a prolonged manner. 24.5 g of the hydrochloride of 2-ethylmethylamino N-(2-mercaptoethyl) acetamide are obtained in the form of a colorless to very pale yellow gel.

The NMR¹H 400 MHz and ¹³C spectra conform to the expected structure.

The thiol dosage by iodometry in an acid medium: Found—4.65 meq/g; Calculated—4.70 meq/g.

Example 10
Preparation of the Dihydrochloride of 3-Aminopropyl N,N-Dimethyl Thioglycinate A suspension of 6.5 g (41 mmoles) of the hydrochloride of N,N-dimethyl glycine acid chloride and 5.25 g (41 mmoles) of the hydrochloride of 3-mercaptopropylamine in 40 cm³ of anhydrous acetonitrile is stirred for 4 hours at reflux under an argon atmosphere.

After cooling to +5° C., the crude thioester is filtered then recrystallized in an ethanol/methanol mixture. After drying at 40° C., 5.3 g of the dihydrochloride of 3-aminopropyl N,N-dimethyl thioglycinate are obtained in the form of a white solid whose melting point (decomposition) is about 215° C.

The NMR¹³C spectrum conforms to the expected structure as does the chloride dosage (Found—8.10 meq/g; Calculated—8.02 meq/g) .

Elemental analysis: $C_7H_{16}N_{20}S.2HCl$

|  | C % | H % | N % | O % | S % | Cl % |
|---|---|---|---|---|---|---|
| Calculated | 33.74 | 7.28 | 11.24 | 6.42 | 12.87 | 28.45 |

-continued

|  | C % | H % | N % | O % | S % | Cl % |
|---|---|---|---|---|---|---|
| Found | 33.68 | 7.18 | 11.17 | 6.19 | 12.92 | 28.25 |

Example 11

Preparation of the Dihydrochloride of 2-(2-Aminoethoxy)ethyl N-Ethyl Thioglycinate A suspension of 5 g (31.8 mmoles) of the hydrochloride of (2-mercaptoethoxy) ethylamine and 5 g (31.6 mmoles) of the hydrochloride of N-ethyl glycine acid chloride in 60 cm$^3$ of anhydrous acetonitrile is heater for 3 hours at reflux with stirring and under an inert atmosphere.

After cooling to +10° C. and filtering, the crude thioester is recrystallized in absolute ethanol. After drying under a vacuum at 50° C., 3.2 g of the dihydrochloride of 2'-(2-aminoethoxy) ethyl N-ethyl thioglycinate are obtained in the form of a white solid whose melting point (decomposition) is about 140° C.

The NMR$^{13}$C spectrum conforms to the expected structure as does the chloride dosage (Found—7.06 meq/g; Calculated—7.03 meq/g).

Elemental analysis: $C_8H_{17}N_2O_2S\cdot 2HCl$

|  | C % | H % | N % | O % | S % | Cl % |
|---|---|---|---|---|---|---|
| Calculated | 34.41 | 7.22 | 10.03 | 11.46 | 11.48 | 25.39 |
| Found | 34.30 | 7.30 | 10.03 | 11.62 | 11.22 | 25.36 |

Example 12

Preparation of the Dihydrochloride of 2-Aminoethyl 4-Dimethylamino Thiobutyrate

A suspension of 3 g (27 mmoles) of cysteamine hydrochloride and 5 g (27 mmoles) of the hydrochloride of the acid chloride of 4-dimethylamino butyric acid in 75 ml of anhydrous acetonitrile is heated at reflux for 5 hours with stirring and under an inert atmosphere.

After cooling to ambient temperature and filtering, the crude thioester is recrystallized in an 8:2 ethanol/isoproylether mixture. After drying under a vacuum, 5.87 g of the dihydrochloride of 2-aminoethyl 4-dimethylamino thiobutyrate are obtained in the form of a white solid whose melting point is 112° C.

The NMH$^1$H and $^{13}$C spectra conform to the expected structure as does the chloride dosage (Found—7.72 meq/g; Calculated—7.75 meq/g).

Example 13

Preparation of the Dihydrochloride of 2-Aminoethyl 2-Ethylamino Thiobutyrate

A suspension of 3.7 g (33 mmoles) of cysteamine hydrochloride and 5 g (33 mmoles) of the hydrochloride of the acid chloride of 2-ethylaminobutyric acid in 100 ml of anhydrous acetonitrile is heated at reflux for 5 hours with stirring and under an inert atmosphere.

After cooling to ambient temperature, and filtering, the crude thioester is recrystallized in a 7:3 isopropyl alcohol/diisopropyl ether mixture. After drying under a vacuum 5.5 g of the dihydrochloride of 2-aminoethyl 2-ethylamino thiobutyrate are obtained in the form of a white solid whose melting point is 121° C.

The NMR$^1$H and $^{13}$C spectra conform to the expected structure as does the chloride dosage (Found—7.55 meq/g; calculated—7.60 meg/g).

The thioesters described in Examples 1, 4, 6, 7, 8, 10, 11 and 12 exhibit good preservation capacity. It is then much more convenient to transform them into thiols in an extemporaneous manner. Thus, by the addition of at least one equivalent of a basic agent such as ammonia, the compounds of these examples lead to the corresponding thiols in an aqueous solution with a titer greater than or equal to 99.8% (iodometry in acid medium).

Examples of Compositions

Example A

In accordance with the invention a reducing composition for the permanent deformation of hair is prepared by mixing the following ingredients:

| A. Reducing Composition | |
|---|---|
| Hydrochloride of 2-dimethylamino N-(2-mercaptoethyl) acetamido | 19 g |
| Monoethanolamine, sufficient amount for pH = 8.5 | |
| Oleocetyl dimethyl hydroxyethyl ammonium chloride | 0.3 g |
| Preservative | 0.2 g |
| Perfume | 0.8 g |
| Demineralized water, sufficient amount for | 100 g |

This composition is applied to moistened hair, previously rolled up on rollers. After letting the composition act on the hair for 15 minutes, the hair is thoroughly rinsed with water. There is then applied to the hair the following oxidizing composition:

| B. Oxidizing composition | |
|---|---|
| H$_2$O | 1.5 g |
| Sodium laurylether sulfate, oxyethylenated with 2 moles of ethylene oxide | 3.75 g |
| Citric acid | 0.5 g |
| Sodium hydrogen phosphate | 0.5 g |
| Perfume | 0.3 g |
| Demineralized water, sufficient amount for | 100 g |

This oxidizing composition is left to react on the hair for about 5 minutes. The rollers are then removed and the hair is thoroughly rinsed with water. After drying under a hood, the hair exhibits beautiful curls.

In accordance with the embodiment described is Example A, a permanent deformation of the hair is carried out using the reducing and oxidizing compositions of the following examples B to M:

Example B

| A. Reducing composition | |
|---|---|
| Hydrochloride of 2-dimethylamino N-(2-mercaptoethyl) acetamide | 21 g |
| Ethylene diamine tetraacetic acid | 0.2 g |
| Triethanolamine, sufficient amount for pH = 6.8 | |
| Lauramine oxide, sold under the trade name "AROMOX DMMCD/W" by Azko | 2.15 g |
| Perfume | 0.6 g |
| Demineralized water, sufficient amount for | 100 g |
| B. Oxidizing composition | |
| H$_2$O$_2$ | 2.0 g |
| Oleocetyl dimethyl hydroxyethyl | 0.3 g |

| | |
|---|---|
| ammonium chloride | |
| Phosphoric acid | 0.5 g |
| p-ethoxyacetanilide (phenacetin) | 0.1 g |
| Protein hydrolyzate | 0.5 g |
| Perfume | 0.5 g |
| Demineralized water, sufficient amount for | 100 g |

Example C

| A. Reducing Composition | |
|---|---|
| Dihydrochloride of 2-aminoethyl N,N-dimethyl thioglycinate | 11 g |
| Ammoniacal solution (20% NH₃) | 4.1 g |
| Monoethanolamine, sufficient amount for pH = 8.0 | |
| Ammonium bicarbonate | 2.0 g |
| Cocoamidopropylbetaine, sold under the trade name "TEGOBETAINE HS" by Goldschmidt | 0.9 g |
| Demineralized water, sufficient amount for | 100 g |
| B. Oxidizing Composition | |
| H₂O₂ | 2.5 g |
| Sodium stannate | 0.03 g |
| Homopolymer of N,N-dimethyl N-2 propenyl-2-propene-1-ammonium chloride (polyquaternium-6), sold under the trade name "MERQUAT 100" by Merck | 1.25 g |
| Citric acid | 0.6 g |
| Perfume | 0.5 g |
| Demineralized water, sufficient, amount for | 1.00 g |

Example D

| A. Reducing Composition | |
|---|---|
| Dihydrochloride of 2-aminoethyl N,N-dimethyl thioglycinate | 17 g |
| N,N'-(2,1-dithiodiethanediyl) bis [2-dimethylamino acetamide] | 5.1 g |
| Pentasodium salt of diethylene triamine pentacetic acid | 0.2 g |
| Monoethyanolamine, sufficient amount for pH = 8.9 | |
| Hydrogenated castor oil oxyethylenated with 60 moles of ethylene oxide, sold under the trade name "NKKOL HCO 60" by Nikko Chemical | 4 g |
| Homopolymer of N,N-dimethyl N-2-propenyl-2-propene-1 ammonium chloride (polyquaternium 7) sold under the trade name "MERQUAT 550" by Merck | 3.8 g |
| Perfume | 0.3 g |
| Demineralized water, sufficient amount for | 100 g |
| B. Oxidizing Composition | |
| H₂O₂ (200 volumes) | 4.8 g |
| Stabilizer | 0.1 g |
| D. Panthenol | 1.0 g |
| 4'-α-dimethyl-α-(4-methyl-3-pentenyl)-3-cyclohexane methanol (Bisabolol), sold under the trade name "DRAGOSANTOL 2/012681" by Dragoco | 0.3 g |
| Lauryl dimethyl amine oxide | 0.7 g |
| Perfume | 0.4 g |
| Lactic acid, sufficient amount for pH = 3.0 | |
| Demineralized water, sufficient amount for | 100 g |

Example E

| A. Reducing Composition | |
|---|---|
| Dihydrochloride of 2-aminoethyl N,N-dimethyl thioglycinate | 3.5 g |
| L-cysteine | 5.0 g |
| Monoethanolamine, sufficient amount for pH = 9.3 | |
| Stearic ester polyethylened with 8 moles of ethylene oxide, sold under the trade name "MYRJ 45" by ICI | 1 g |
| Preservative | 0.4 g |
| Perfume | 0.3 g |
| Demineralized water, sufficient amount for | 100 g |
| B. Oxidizing composition | |
| H₂O₂ | 2.5 g |
| Sodium stannate | 0.02 g |
| Ammonium lauryl sulfate | 1.5 g |
| Protein hydrolyzate | 0.6 g |
| Citric acid | 0.5 g |
| Perfume | 0.4 g |
| Demineralized water, sufficient amount | 100 g |

Example F

| A. Reducing Composition | |
|---|---|
| Dihydrochloride of 2-aminoethyl N,N-dimethyl thioglycinate | 2.5 g |
| N-acetylcysteamine | 6.0 g |
| Ammoniacal solution, sufficient amount for pH = 8.0 | |
| Ammoniun bicarbonate | 2.0 g |
| Homopolymer of N,N-dimethyl N-2-propenyl-2 propene-1 ammonium chloride (polyquaternium-6) sold under the trade name "MERQUAT 100" by Merck | 2.5 g |
| Collagen hydrolyzate | 0.5 g |
| Oleocetyldimethyl hydroxyethyl ammonium chloride | 1.0 g |
| Perfume | 0.8 g |
| Demineralized water, sufficient amount for | 100 g |
| B. Oxidizing Composition | |
| H₂O₂ (200 volumes) | 4.8 g |
| Stabilizer | 0.1 g |
| D. Panthenol | 1.0 g |
| 4'-α-dimethyl-α-(4-methyl-3-pentenyl)-3-cyclohexene methanol (Bisabolol) sold under the trade name "DRAGOSANTOL 2/012681" by Dragoco | 0.3 g |
| Lauryl dimethyl amine oxide | 0.7 g |
| Perfume | 0.4 g |
| Lactic acid, sufficient amount for pH = 3.0 | |
| Demineralized water, sufficient amount for | 100 g |

Example G

| A. Reducing Composition | |
|---|---|
| Dihydrochloride of 2-aminoethyl N,N-dimethyl thioglycinate | 2.0 g |
| N-propionyl cysteamine | 6.5 g |
| Monoethanolamine, sufficient amount for pH = 8.5 | |
| Cetyl trimethyl ammonium chloride | 1.0 g |
| Perfume | 0.6 g |
| Preservative | 0.15 g |
| Demineralized water, sufficient amount for | 100 g |
| B. Oxidizing composition | |
| Sodium bromate | 8 g |
| Triethanolamine, sufficient amount for pH = 8.0 | |
| Hydrated monosodium phosphate (12H₂O) | 0.3 g |
| Hydrated trisodium phosphate (2H₂O) | 0.5 g |
| Cocoamidopropylbetaine, sold under the trade name "TEGOBETAINE HS" by Goldschmidt | 1.0 g |
| Perfume | 0.4 g |
| Demineralized water, sufficient amount for | 100 g |

Example H

| A. Reducing Composition | |
|---|---|
| Dihydrochloride of 2-aminoethyl N,N-dimethyl thioglycinate | 2.0 g |
| Cysteamine hydrochloride | 5.2 g |
| Monoethanolamine, sufficient amount for pH = 9.5 | |
| Cetyl trimethyl ammonium chloride | 1.0 g |
| Perfume | 0.6 g |
| Preservative | 0.15 g |
| Demineralized water, sufficient amount for | 100 g |
| B. Oxidizing composition | |
| Sodium bromate | 8 g |
| Triethanolamine, sufficient amount for pH = 8.0 | |
| Hydrated monosodium phosphate (12H$_2$O) | 0.3 g |
| Hydrated trisodium phosphate (2H$_2$O) | 0.5 g |
| Cocoamidopropylbetaine, sold under the trade name "TEGOBETAINE HS" by Goldschmidt | 1.0 g |
| Perfume | 0.4 g |
| Demineralized water, sufficient amount for | 100 g |

Example I

| A. Reducing Composition | |
|---|---|
| Dihydrochloride of 2-aminoethyl N-ethyl N-methyl thioglycinate | 8 g |
| Laurylamino oxide, sold under the trade name "AROMOX DMMCD/W", by Akzo | 2 g |
| Ethylene diamine tetraacetic acid | 0.15 g |
| Perfume, sufficient amount | |
| Monoethanolamine, sufficient amount for pH = 8.1 | |
| Demineralized water, sufficient amount for | 100 g |
| B. Oxidizing composition | |
| H$_2$O$_2$ | 2 g |
| Sodium stannate | 0.015 g |
| Ammonium lauryl sulfate | 1.4 g |
| Protein hydrolyzate | 0.6 g |
| Citric acid | 0.5 g |
| Perfume, sufficient amount | |
| Demineralized water, sufficient amount for | 100 g |

Example J

| A. Reducing Composition | |
|---|---|
| Dihydroxychloride of 2-aminoethyl N-ethylthioglycinate | 19 g |
| Laurylamine oxide, sold under the trade name "AROMOX DMMCD/W" by Akzo | 2 g |
| Homopolymer of N,N-dimethyl N-2 propenyl-2 propene-1 chloride (polyquaternium-6), sold under the trade name "MERQUAT 100" by Merck | 1.10 g |
| Perfume, sufficient amount | |
| Ammonia (20%), sufficient amount for pH = 8.6 | |
| Demineralized water, sufficient amount for | 100 g |
| B. Oxidizing Composition | |
| This composition is identical to that of Example I. | |

Example K

| A. Reducing Composition | |
|---|---|
| Dihydrochloride of 2-aminoethyl N,N-dimethyl thioglyciante | 12 g |
| Stearic ester polyethylened with 8 moles of ethylene oxide, sold under the trade name "MYRJ 45" by ICI | 0.85 g |
| Preservative | 0.35 g |
| Perfume, sufficient amount | |
| Monoethanolamine, sufficient amount for pH = 8.8 | |
| Demineralized water, sufficient amount for | 100 g |
| B. Oxidizing Composition | |
| This composition is identical to that in Example I. | |

Example L

| A. Reducing composition | |
|---|---|
| Dihyrochloride of 2-aminoethyl N-methyl thioglycinate | 20 g |
| Laurylamine oxide, sold under the trade name "AROMOX DMMCD/W" by Akzo | 2 g |
| Preservative | 0.15 g |
| Perfume, sufficient amount | |
| Monoethanolamine, sufficient amount for pH = 7.8 | |
| Demineralized water, sufficient amount for | 100 g |
| B. Oxidizing Composition | |
| This composition is identical to that in Example I. | |

Example M

| A. Reducing Composition | |
|---|---|
| Dihydrochloride of 2-aminoethyl N,N-diethyl thioglycinate | 7.2 g |
| Oleocetyl dimethyl hydroxyethyl ammonium chloride | 0.3 g |
| Preservative | 0.15 g |
| Perfume, sufficient amount | |
| Ammonia, sufficient amount for pH = 8.0 | |
| Demineralized water, sufficient amount for | 100 g |
| B. Oxidizing Composition | |
| This composition is identical to that of Example I. | |

We claim:

1. A compound having the general formula II

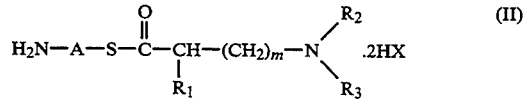

wherein

A represents the divalent radical —(CH$_2$)$_n$— wherein n is a whole number ranging from 2 to 5 or the divalent radical —(CH$_2$)$_2$—O—(CH$_2$)$_2$—, m is equal to 0, 1 or 2, R$_1$ represents hydrogen or a linear or branched lower alkyl having 1–5 carbon atoms, R$_2$ and R$_3$, each independently, represent hydrogen or linear or branched lower alkyl having 1–4 carbon atoms, with the proviso that R$_2$ and R$_3$ do not simultaneously represent hydrogen, and X represents Cl or Br.

2. The compound of claim 1 selected from the group consisting of the dihydrochloride of 2-aminoethyl N,N-dimethyl thioglycinate, the dihydrochloride of 3-aminopropyl N,N-dimethyl thioglycinate, the dihydrochloride of 5-aminopentyl N,N-dimethyl thioglycinate, the dihydrochloride of 2'-(2-aminoethoxy) ethyl N,N-dimethyl thioglycinate,
the dihydrochloride of 2-aminoethyl N,N-diethyl thioglycinate,
the dihydrochloride of 3-aminopropyl N,N-diethyl thioglycinate,
the dihydrochloride of 5-aminopentyl N,N-diethyl thioglycinate,
the dihydrochloride of 2'-(2-aminoethoxy) ethyl N,N-ethyl thioglycinate,
the dihydrochloride of 2-aminoethyl N-methyl thioglycinate,
the dihydrochloride of 3-aminopropyl N-methyl thioglycinate,
the dihydrochloride of 5-aminopentyl N-methyl thioglycinate,
the dihydrochloride of 2'-(2-aminoethoxy) ethyl N-methyl thioglycinate,
the dihydrochloride of 2-aminoethyl N-ethyl thioglycinate,
the dihydrochloride of 3-aminopropyl N-ethyl thioglycinate,
the dihydrochloride of 5-aminopentyl N-ethyl thioglycinate,
the dihydrochloride of 2'-(2-aminoethoxy) ethyl N-ethyl thioglycinate,
the dihydrochloride of 2-aminoethyl N-ethyl-N-methyl thioglycinate,
the dihydrochloride of 2-aminoethyl N-propyl thioglycinate,
the dihydrochloride of 2-aminoethyl N-isopropyl thioglycinate,
the dihydrochloride of 2-aminoethyl N-butyl thioglycinate,
the dihydrochloride of 2-aminoethyl 3-dimethyl amino thiopropionate,
the dihydrochloride of 3-aminopropyl-3-dimethylamino thiopropionate,
the dihydrochloride of 5-aminopentyl 3-dimethylamino thiopropionate,
the dihydrochloride of 2'-(2-aminoethoxy) ethyl 3-dimethylamino thiopropionate,
the dihydrochloride of 2-aminoethyl 3-methylamino thioprionate,
the dihydrochloride of 3-aminopropyl 3-methylamino thiopropionate,
the dihydrochloride of 5-aminopentyl 3-methylamino thiopropionate,
the dihydrochloride of 2'-(2-aminoethoxy) ethyl 3-methylamino thiopropionate,
the dihydrochloride of 2-aminoethyl N,N-dimethyl thioalaninate,
the dihydrochloride of 3-aminopropyl N,N-dimethyl thioalaninate,
the dihydrochloride of 5-aminopentyl N,N-dimethyl thioalaninate,
the dihydrochloride of 2'-(2-aminoethoxy) ethyl N,N-dimethyl thioalaninate,
the dihydrochloride of 2-aminoethyl N-methyl thioalaninate,
the dihydrochloride of 2-aminoethyl N-ethyl thioalaninate,
the dihydrochloride of 2-aminoethyl N-isopropyl thioalaninate,
the dihydrochloride of 2-aminoethyl 2-methylamino thiobutyrate,
the dihydrochloride of 2-aminoethyl 4-dimethyl aminothiobutyrate,
the dihydrochloride of 3-aminopropyl 4-dimethylamino thiobutyrate,
the dihydrochloride of 5-aminopentyl 4-dimethylamino thiobutyrate,
the dihydrochloride of 2'-(2-aminoethoxy) ethyl 4-dimethylamino thiobutyrate,
the dihydrochloride of 2-aminoethyl 4-methylamino thiobutyrate,
the dihydrochloride of 2-aminoethyl 4-ethylamino thiobutyrate,
the dihydrochloride of 2-aminoethyl N,N-dimethylamino thiovalinate,
the dihydrochloride of 2-aminoethyl N,N-dimethylamino thioleucinate,
the dihydrochloride of 2-aminoethyl N-methylamino thioleucinate,
the dihydrochloride of 2-aminoethyl N,N-dimethylamino thioisoleucinate,
the dihydrochloride of 2-aminoethyl N-methylamino thioisoleucinate,
the dihydrochloride of 2-aminoethyl thiopipecolinate and the dihydrochloride of 2-aminoethyl hexahydroisothionicotinate.

* * * * *